US011141172B2

(12) United States Patent
Laird, Jr. et al.

(10) Patent No.: US 11,141,172 B2
(45) Date of Patent: Oct. 12, 2021

(54) METHOD AND APPARATUS FOR LOCKING A DRILL GUIDE IN A POLYAXIAL HOLE

(71) Applicant: GLOBUS MEDICAL, INC., Audubon, PA (US)

(72) Inventors: David Laird, Jr., Brandamore, PA (US); Gabrielle Zingalis, Philadelphia, PA (US); Andrew Davison, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 279 days.

(21) Appl. No.: 16/373,676

(22) Filed: Apr. 3, 2019

(65) Prior Publication Data

US 2019/0314042 A1 Oct. 17, 2019

Related U.S. Application Data

(60) Provisional application No. 62/655,934, filed on Apr. 11, 2018.

(51) Int. Cl.
*A61B 17/17* (2006.01)
*A61B 17/00* (2006.01)

(52) U.S. Cl.
CPC .... *A61B 17/17* (2013.01); *A61B 2017/00477* (2013.01)

(58) Field of Classification Search
CPC ... A61B 17/17; A61B 17/1728; A61B 17/808; A61B 17/8872
See application file for complete search history.

(56) References Cited

U.S. PATENT DOCUMENTS

| 1,105,105 A | 7/1914 | Sherman |
| 2,486,303 A | 10/1949 | Longfellow |
| 3,463,148 A | 8/1969 | Treace |
| 3,695,259 A | 10/1972 | Yost |
| 3,716,050 A | 2/1973 | Johnston |
| 4,219,015 A | 8/1980 | Steinemann |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |

(Continued)

FOREIGN PATENT DOCUMENTS

| CN | 201987653 U | 9/2011 |
| CN | 202313691 U | 7/2012 |

(Continued)

*Primary Examiner* — Anu Ramana

(57) ABSTRACT

Devices, systems, and methods for locking a drill guide into a polyaxial hole while maintaining the form and function of the polyaxial hole are provided herein. In some embodiments, the drill guide includes a hollow outer body extending from a proximal end to a distal end and having a slot disposed proximate the proximate end, wherein the distal end is configured as a reverse collet having a plurality of prongs; an inner body having a central channel extending therethrough; and a lever coupled to the inner body through the slot, wherein the slot is shaped such that rotation of the lever results in motion along a central axis of the drill guide, and wherein a distal end of the inner body is configured to prevent radially inward deflection of the plurality of prongs when the inner body is in a lowermost position.

20 Claims, 5 Drawing Sheets

(56) References Cited

U.S. PATENT DOCUMENTS

| | | | |
|---|---|---|---|
| 4,781,183 A | 11/1988 | Casey et al. |
| 4,867,144 A | 9/1989 | Karas et al. |
| 4,923,471 A | 5/1990 | Morgan |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,851,207 A | 12/1998 | Cesarone |
| 5,925,048 A | 7/1999 | Ahmad et al. |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,118,848 B2 | 2/2012 | Ducharme et al. |
| 8,162,950 B2 * | 4/2012 | Digeser ............... A61B 17/1728 606/96 |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |

(56) References Cited

U.S. PATENT DOCUMENTS

| | | |
|---|---|---|
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| D765,851 S | 9/2016 | Early et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,750,512 B2 * | 9/2017 | Jerke ............... A61B 17/1728 |
| 9,801,670 B2 | 10/2017 | Hashmi et al. |
| 9,814,504 B2 | 11/2017 | Ducharme et al. |
| 2002/0045901 A1 | 4/2002 | Wagner et al. |
| 2004/0097937 A1 | 5/2004 | Pike et al. |
| 2005/0038444 A1 | 2/2005 | Binder, Jr. et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0036254 A1 * | 2/2006 | Lim ............... A61B 17/7086 606/86 R |
| 2006/0149265 A1 | 7/2006 | James et al. |
| 2006/0241607 A1 | 10/2006 | Myerson et al. |
| 2007/0173840 A1 | 7/2007 | Huebner |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0287225 A1 | 11/2009 | Olsen et al. |
| 2009/0299369 A1 | 12/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0203227 A1 | 8/2012 | Martin |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet al. |
| 2013/0211463 A1 | 8/2013 | Mizuno et al. |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0183990 A1 | 6/2016 | Koizumi et al. |

(56) References Cited

U.S. PATENT DOCUMENTS

| | | |
|---|---|---|
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0215931 A1 | 8/2017 | Cremer et al. |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| FR | 2846870 A1 | 5/2004 |
| FR | 2928259 A1 | 9/2009 |
| JP | 2003210478 A | 7/2003 |
| JP | 2007-502171 A | 2/2007 |
| TW | 201316942 A | 5/2013 |
| WO | 2016079504 A1 | 5/2016 |

\* cited by examiner

METHOD AND APPARATUS FOR LOCKING A DRILL GUIDE IN A POLYAXIAL HOLE

RELATED APPLICATIONS

This application claims priority to U.S. Provisional Patent Application No. 62/655,934, filed Apr. 11, 2018, the contents of which are hereby incorporated by reference in its entirety.

FIELD

The present disclosure relates to surgical devices, and more particularly, stabilization systems, for example, for trauma applications.

BACKGROUND

Bone fractures are often repaired by internal fixation of the bone, such as diaphyseal bone, using one or more plates. The plate is held against the fractured bone with screws, for example, which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. There may be a desire to use locking screws, non-locking screws, or a combination of both that are able to compress the bone. Of course, the designs of the plates, types of screws, and locking and/or non-locking capabilities may vary based on the location and type of fracture.

In some cases, plates having polyaxial holes may be used to provide increased flexibility with regards to screw orientation. However, with such polyaxial holes, locking of the screw may be difficult. As such, features may be included in the holes to provide surfaces against which the screw can lock. However, there is a need for a method for aligning a drill bit to the nominal axis of a polyaxial hole and locking the drill guide in such a hole without compromising the structure of the hole. Such a hole cannot be threaded into via a threaded drill guide because doing so would jeopardize the locking capabilities of the polyaxial hole.

SUMMARY

To meet this and other needs, devices, systems, and methods for locking a drill guide into a polyaxial hole while maintaining the form and function of the polyaxial hole are provided herein. In some embodiments, the drill guide includes a hollow outer body extending from a proximal end to a distal end and having a slot disposed proximate the proximal end, wherein the distal end is configured as a reverse collet having a plurality of prongs; an inner body having a central channel extending therethrough; and a lever coupled to the inner body through the slot, wherein the slot is shaped such that rotation of the lever results in motion along a central axis of the drill guide, and wherein a distal end of the inner body is configured to prevent radially inward deflection of the plurality of prongs when the inner body is in a lowermost position.

In some embodiments, a method of locking a drill guide in a hole includes inserting the drill guide into the hole; pushing the distal end of the outer body beyond a shoulder of the hole, wherein the shoulder pushes the plurality of prongs radially inwardly upon contact, and wherein the plurality of prongs return to a resting position after the distal end is pushed beyond the shoulder; and rotating the lever to move the inner body to a lowermost position in which a distal end of the inner body is disposed between the plurality of prongs to prevent radially inward deflection of the plurality of prongs.

In some embodiments, a drill guide includes a hollow outer body extending from a proximal end to a distal end and having a slot disposed proximate the proximal end, wherein the distal end is configured as a reverse collet having a plurality of prongs; an inner body having a central channel extending therethrough; a spring disposed within the hollow outer body and beneath a portion of the inner body, wherein the spring biases the inner body in a direction away from the plurality of prongs; a cap coupled to the proximal end of the hollow outer body and having a through hole disposed through an upper portion of the cap in communication with the central channel, wherein the through hole is configured to allow passage of a drill bit into the central channel; a handle coupled to the hollow outer body to allow a user to grip the drill guide; and a lever coupled to the inner body through the slot, wherein the slot is shaped such that rotation of the lever results in motion along a central axis of the drill guide, and wherein a distal end of the inner body is configured to prevent radially inward deflection of the plurality of prongs when the inner body is in a lowermost position.

BRIEF DESCRIPTION OF THE DRAWING

A more complete understanding of the present invention, and the attendant advantages and features thereof, will be more readily understood by reference to the following detailed description when considered in conjunction with the accompanying drawings wherein.

DETAILED DESCRIPTION

Figure 1A:
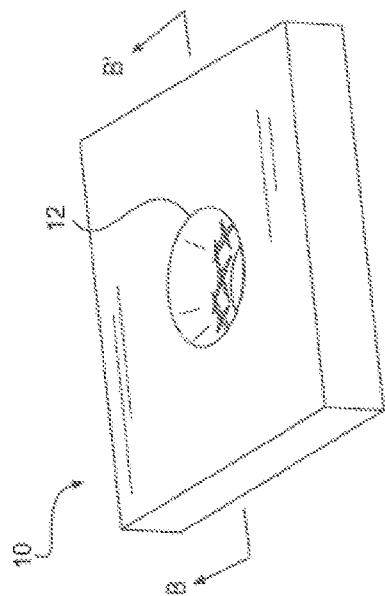
FIG. 1A depicts an isometric view of a plate having a polyaxial hole with which a drill guide in accordance with at least some embodiments of the present invention may be utilized.

Embodiments of the disclosure are generally directed to devices, systems, and methods for aligning and locking a drill guide into a polyaxial hole while maintaining the form and function of the polyaxial hole. Specifically, embodiments are directed to a drill guide configured to align a drill bit with a nominal axis/trajectory of a polyaxial screw hole. The inventive drill guide may be used with bone plates with locking and/or non-locking fasteners for dynamic compression of the bone. The hole designs may allow for polyaxial locking of the fasteners. The inventive drill guide advantageously provides for one-handed operation with quick and reliable locking capabilities. The inventive drill guide is also ergonomic and its design is streamlined.

The plates may be adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plate may be curved, contoured, straight, or flat. The plate may have a head portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated.

The embodiments of the disclosure and the various features and advantages details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Figure 1B:
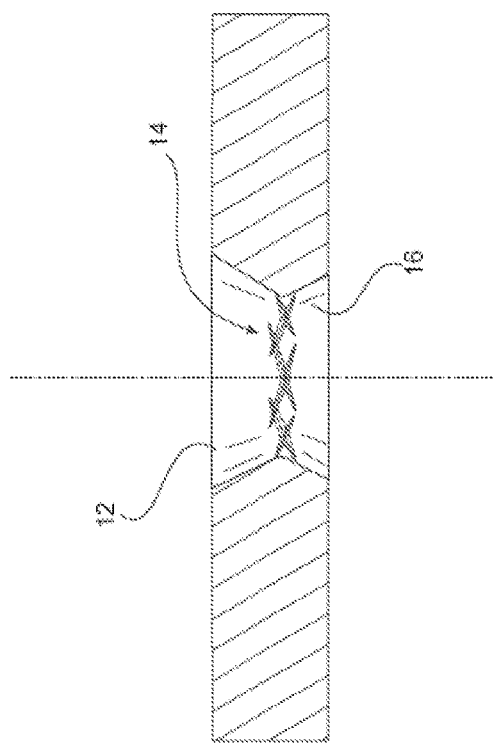
FIG. 1B depicts a cross-sectional view of the plate of FIG. 1A taken along line B-B'.

Referring now to the drawings, FIGS. 1A and 1B depict an isometric view and a cross-sectional view, respectively, of a plate 10 including at least one opening such as, for example, a polyaxial hole 12. The polyaxial hole 12 extends through the plate 10 is configured to accept a locking fastener (not shown) that is able to dynamically compress the bone and/or affix the plate 10 to the bone.

As shown more clearly in FIG. 1B, the polyaxial hole 12 may have one or more locking features designed to engage with the locking fastener such as, for example, wind-swept cuts 14 discreetly patterned in two directions. The polyaxial hole geometry may be used in bone plates 10 to utilize polyaxial locking screws that can achieve dynamic compression. Although only one polyaxial hole 12 is shown, the plate 10 may comprise any suitable number of polyaxial holes 12 in any suitable configuration.

The polyaxial hole 12 cannot be threaded into via a threaded drill guide because doing so would jeopardize the locking capabilities of the polyaxial hole 12. That is, threading into the polyaxial hole 12 would damage the wind-swept cuts 14, thus negatively impacting the locking capabilities of the polyaxial hole 12. As such, the inventors have discovered an improved drill guide 200 that overcomes the need to thread into a polyaxial hole.

Figure 2:
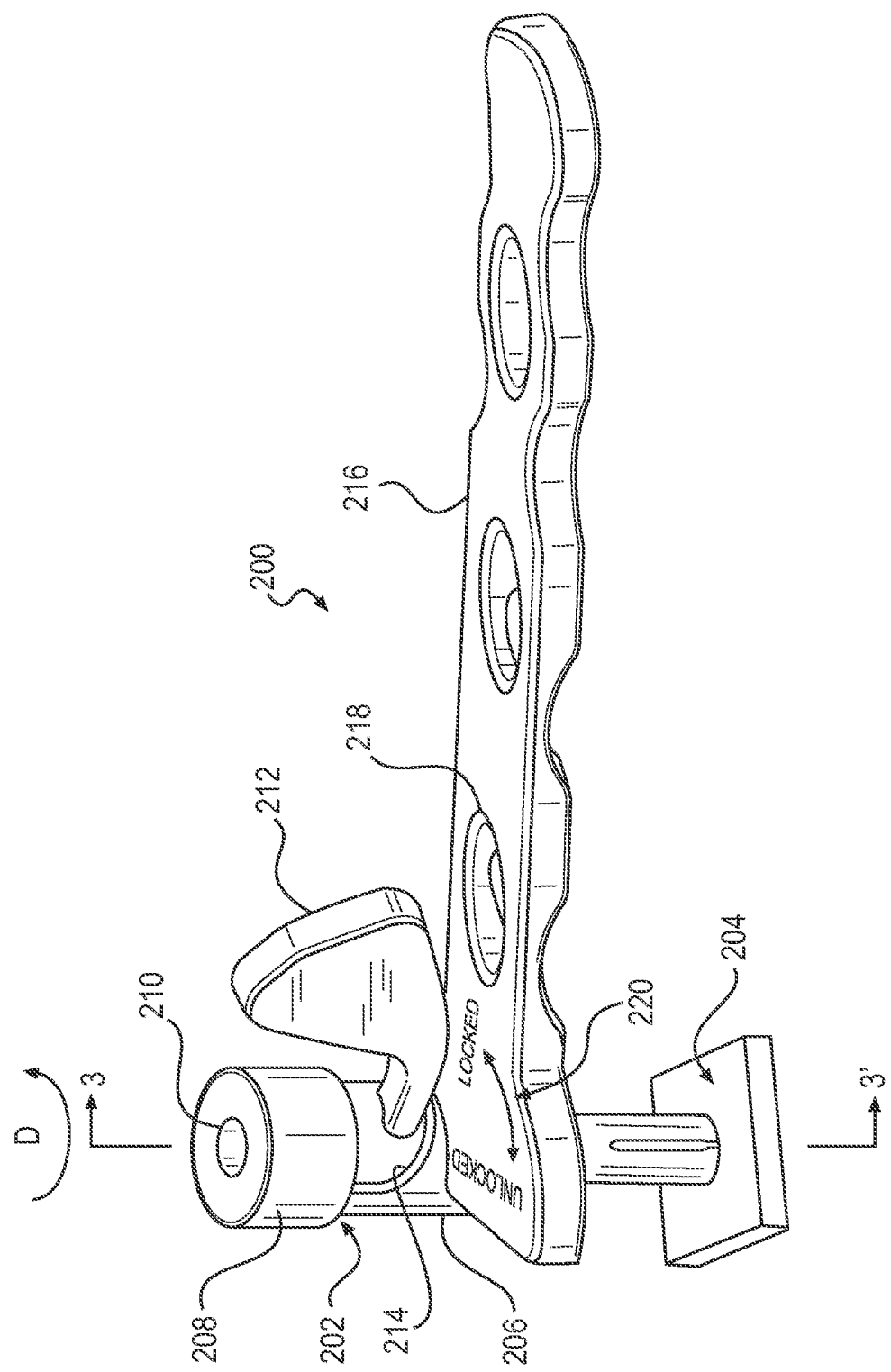
FIG. 2 depicts an isometric view of a drill guide in accordance with at least some embodiments of the present invention.
Figure 3:
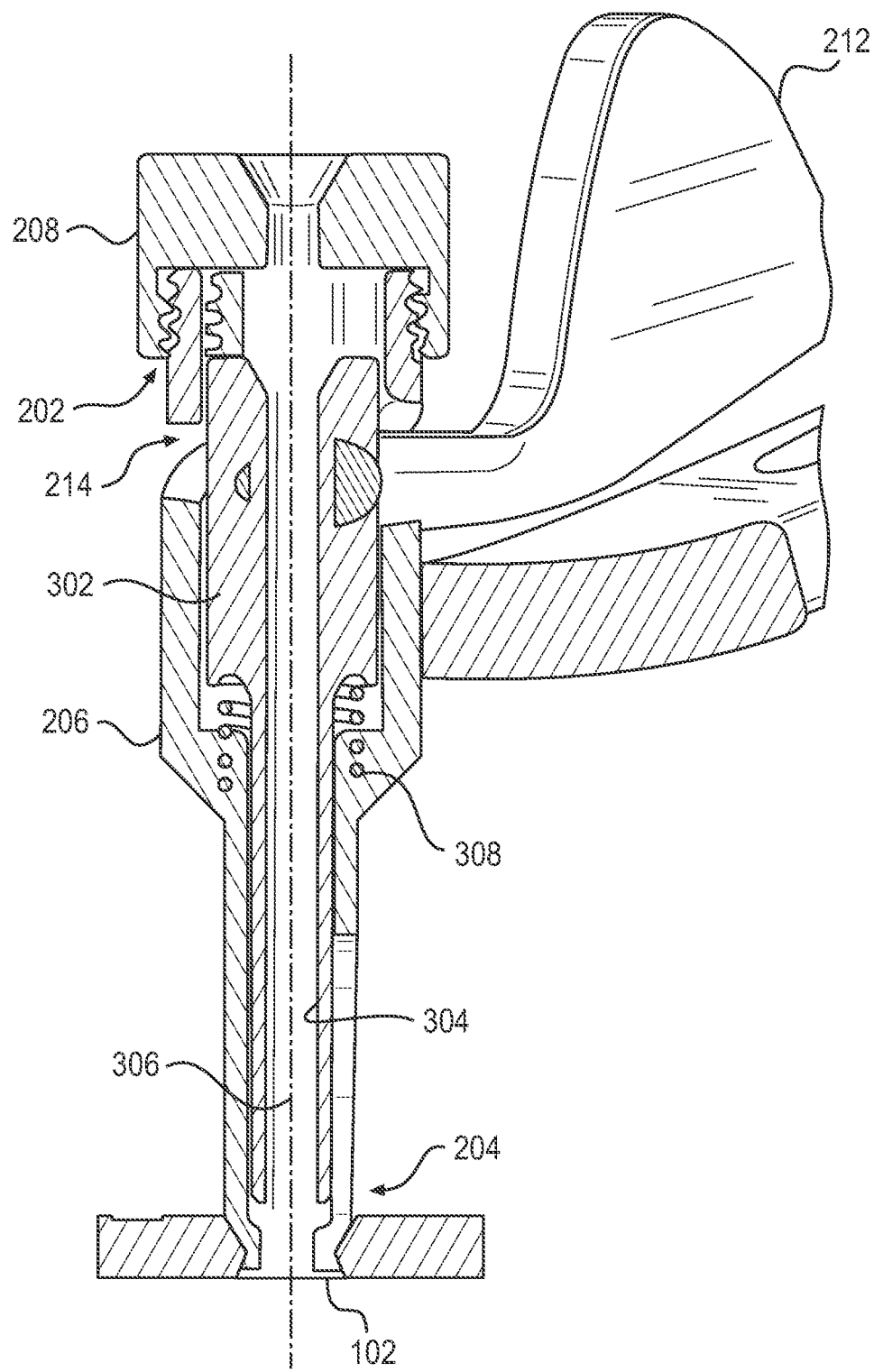
FIG. 3 depicts a cross-sectional view of the drill guide of FIG. 2 taken along line 3-3'.
Figure 4:
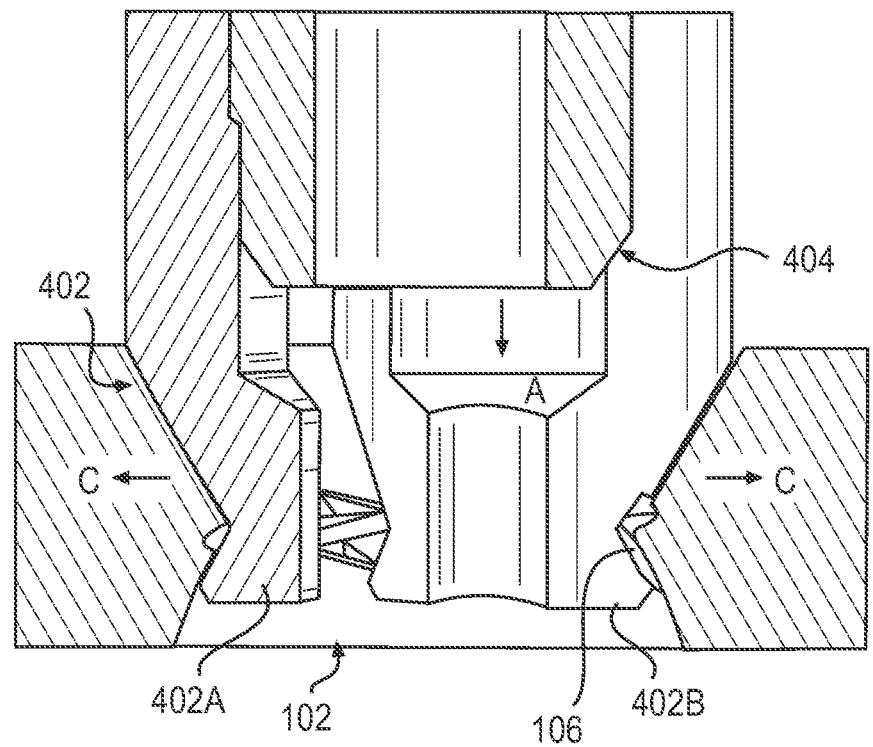
FIG. 4 depicts a close-up cross-sectional view of a drill guide inserted into a polyaxial hole in accordance with at least some embodiments of the present invention.

Referring to FIGS. 2-4, the drill guide 200 extends from a proximal end 202 to a distal end 204 and includes an outer body 206 and an inner body 302 (shown in FIG. 3) disposed within and concentric with the outer body 206. The outer body 206 is substantially hollow and houses the inner body 302. A cap 208 may be disposed and locked onto the proximal end 204 of the outer body 206 and includes a through hole 210 disposed through an upper portion of the cap 210. The through hole 210 is configured to allow the passage of a drill bit (not shown) to extend into the interior of the drill guide 200. In some embodiments, the drill guide 200 may further include a handle 216 coupled to the outer body 206. The handle 216 may include one or more holes 218 to facilitate placement of additional tools such as, for example, a guide wire. In some embodiments, the handle 216 is fixedly coupled to the outer body 206. In some embodiments, the handle 216 is alternatively removably coupled to the outer body 206.

As depicted in FIG. 3, the inner body 302 is tubular an includes a central channel 304 extending along a central axis 306 of the drill guide 200. The inner body 302 is configured to receive a drill bit extending through the central channel 304 and to align the drill bit with the central axis 103 of the hole 102. In embodiments in which it is desirable for the screw (not shown) extending through the hole 102 to not be aligned with the central axis 103 of the hole 102, the drill guide 200 may alternatively be configured to align the drill bit with a different trajectory (i.e., the central axis 306 is aligned with the desired orientation of the screw to be utilized in the hole 102).

As shown more clearly in FIG. 4, the distal end 204 of the drill guide 200 may be configured as a reverse collet 402 so that when the drill guide 200 is pushed into the hole 102, a plurality of prongs 402A,B,C (only A and B shown in cross-section of FIG. 4) of the reverse collet 402 are forced radially inwardly (opposite the direction of arrows C) by the shape of the hole 102 (e.g., a shoulder 106). Subsequently, when the drill guide 200 is pushed further into the hole 102, the prongs 402A,B,C return to their original position, as depicted in FIG. 4. It should be noted that although the description of the reverse collet 402 includes three prongs, the reverse collet may alternative include fewer or more prongs.

Referring now to FIGS. 2-4, in some embodiments, the drill guide 200 may include a lever 212 a distal end of which is coupled to the inner body 302 through a slot 214 formed in the outer body 206. The slot 214 is shaped such that when the lever 212 is turned in a predetermined direction (indicated by arrow D), the inner body 302 is moved downwards, as indicated by arrow A in FIG. 4. The downward motion of the inner body 302 moves a distal end 404 of the inner body 302 into an area between the prongs 402A,B,C, thus forcing the prongs 402A,B,C radially outwardly, as indicated by arrows C, which prevents the prongs from retracting radially inwardly. As a result, the drill guide 200 becomes locked in the hole 102. Thus, a rigid locking of the drill guide 200 is provided which also advantageously avoids damage of the screw locking features of the hole 102. The rigid locking also ensures that the drill guide 200 remains properly aligned with the desired screw trajectory to ensure drilling always occurs at the correct orientation. It should be noted that use of a lever to move the inner body 302 is only exemplary and any means of moving the inner body downwardly to lock the drill guide 200 is contemplated.

In some embodiments, the drill guide 200 may include a spring 308 to bias the inner body 302 upwardly, such that the turning of the lever 212 to lower the inner body 302 acts against a bias of the spring 308. In some embodiments, the handle 216 may include a graphic 220 to indicate in which direction movement of the lever will lock and unlock the drill guide 200 in the hole.

Figure 5:
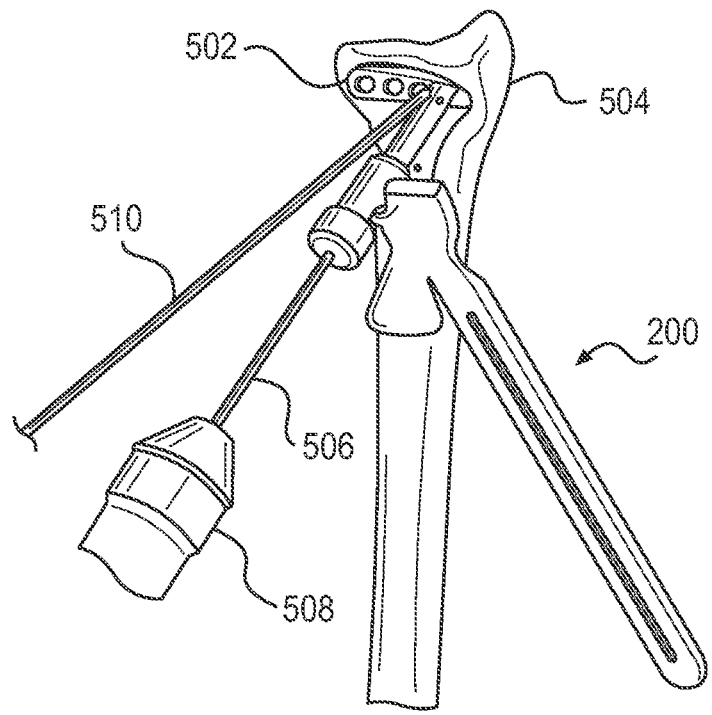
FIG. 5 depicts a perspective view of a drill guide used to introduce a plate into a surgical field and as a drill guide in accordance with some embodiments of the present invention.

In some embodiments, the rigid locking provided by the drill guide 200 may advantageously also allow for the use of the drill guide 200 to introduce a device (e.g., a fixation plate) into a surgical area, as shown, for example, in FIG. 5. In the example shown in FIG. 5, the drill guide 200 is locked into a hole (not visible) of a plate 502. The drill guide may be used to transport and position the plate 502 at a surgical site such as, for example, a bone 504. After the plate 502 is positioned as desired, the drill bit 506 of a drill 508 may be inserted into the drill guide 200 to drill a hole into the bone 504. In addition, a guide wire 510 may also be inserted into the plate 504 to guide a screw (not shown) into the bone 504.

Figure 6:
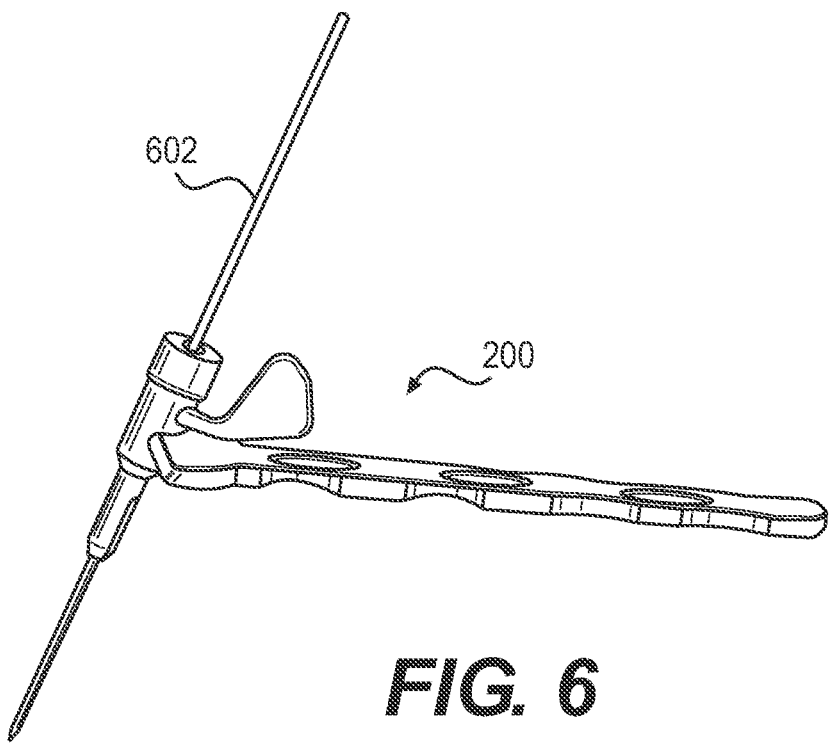
FIG. 6 depicts a side perspective view of a drill guide used as a k-wire guide in accordance with some embodiments of the present disclosure.

As shown in FIG. 6, in some embodiments, the drill guide 200 may also be used to insert a k-wire 602 for provisional fixation.

Figure 7:
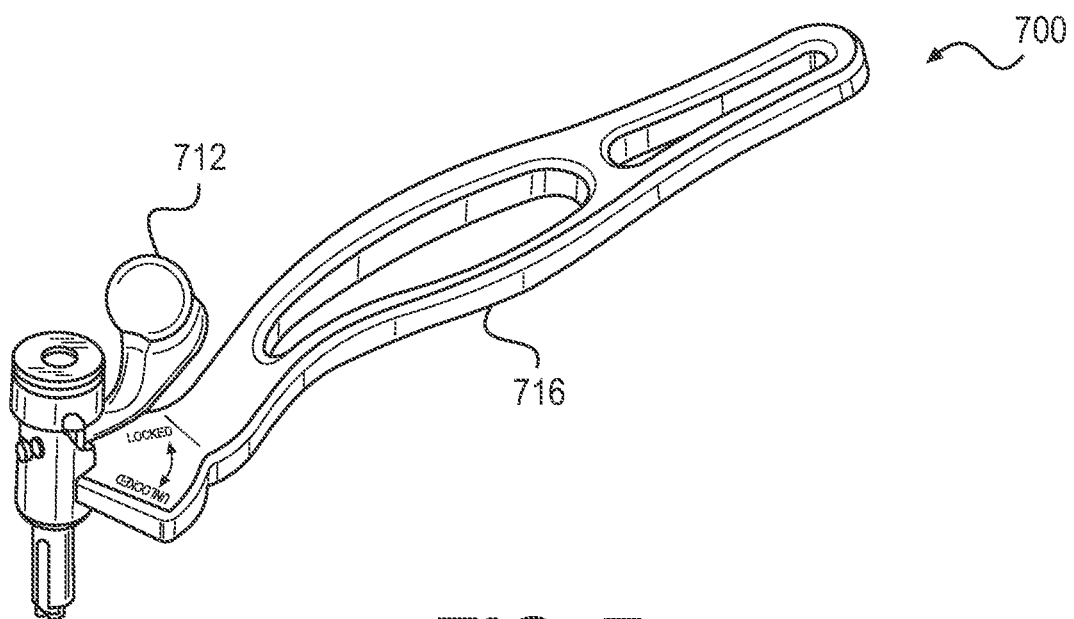
FIG. 7 depicts an isometric view of a drill guide in accordance with at least some embodiments of the present invention.

FIG. 7 depicts an embodiment of a drill guide 700 in accordance with embodiments of the present disclosure. The drill guide 700 is substantially similar to the drill guide 200 described above. In some embodiments, the drill guide 700 includes a handle 716 that is similar to the handle 216 described above except that the handle 716 has an improved ergonomic design configured to fit the general contours of a user's hand. In some embodiments, the drill guide 700 may also include a lever 712 that functions similarly to the lever 212. In this embodiment, the lever 712 may have a spherical shape for improved grasping by a user.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A drill guide, comprising:
   a hollow outer body extending from a proximal end to a distal end and having a slot disposed proximate the proximal end, wherein the distal end is configured as a reverse collet having a plurality of prongs;
   an inner body having a central channel extending therethrough; and
   a lever extending through the slot and coupled to the inner body, wherein the slot is shaped such that rotation of the lever results in the inner body moving along a central axis of the drill guide within the hollow outer body, and wherein a distal end of the inner body is configured to prevent radially inward deflection of the plurality of prongs when a distal end of the inner body is moved into a distal end portion of the hollow outer body.

2. The drill guide of claim 1, further comprising:
   a spring disposed within the hollow outer body and beneath a portion of the inner body, wherein the spring biases the inner body in a direction away from the plurality of prongs.

3. The drill guide of claim 1, further comprising:
   a handle coupled to the hollow outer body to allow a user to grip the drill guide.

4. The drill guide of claim 3, wherein the handle includes one or more holes configured to facilitate placement of a tool through the one or more holes.

5. The drill guide of claim 3, wherein the handle is fixedly coupled to the hollow outer body.

6. The drill guide of claim 3, wherein the handle is removably coupled to the hollow outer body.

7. The drill guide of claim 1, wherein the plurality of prongs are configured to deflect radially inwardly when the prongs are inserted into a hole.

8. The drill guide of claim 1, wherein the lever has a spherical shape.

9. The drill guide of claim 1, further comprising:
   a cap coupled to the proximal end of the hollow outer body and having a through hole disposed through an upper portion of the cap in communication with the central channel, wherein the through hole is configured to allow passage of a drill bit into the central channel.

10. A method of locking a drill guide in a hole, comprising:
    inserting the drill guide into the hole, wherein the drill guide comprises:
       a hollow outer body extending from a proximal end to a distal end and having a slot disposed proximate the proximate end, wherein the distal end is configured as a reverse collet having a plurality of prongs;
       an inner body having a central channel extending therethrough; and
       a lever extending through the slot and coupled to the inner body, wherein the slot is shaped such that rotation of the lever results in the inner body moving along a central axis of the drill guide;
    moving the distal end of the hollow outer body beyond a shoulder of the hole provided in a plate, wherein the shoulder pushes the plurality of prongs radially inwardly upon contact, and wherein the plurality of prongs return to a resting position after the distal end is pushed beyond the shoulder; and
    rotating the lever to move the inner body to a lowermost position in which a distal end of the inner body is disposed between the plurality of prongs to prevent radially inward deflection of the plurality of prongs.

11. The method of claim 10, wherein the drill guide further comprises:
    a spring disposed within the hollow outer body and beneath a portion of the inner body, wherein the spring biases the inner body in a direction away from the plurality of prongs.

12. The method of claim 10, wherein the drill guide further comprises:
    a handle coupled to the hollow outer body to allow a user to grip the drill guide.

13. The method of claim 12, wherein the handle includes one or more holes configured to facilitate placement of a tool through the one or more holes.

14. The method of claim 12, wherein the handle is fixedly coupled to the hollow outer body.

15. The method of claim 12, wherein the handle is removably coupled to the hollow outer body.

16. The method of claim 10, wherein the plurality of prongs are configured to deflect radially inwardly when the prongs are inserted into a hole.

17. The method of claim 10, wherein the lever has a spherical shape.

18. The method of claim 10, wherein the drill guide further comprises:

a cap coupled to the proximal end of the hollow outer body and having a through hole disposed through an upper portion of the cap in communication with the central channel, wherein the through hole is configured to allow passage of a drill bit into the central channel.

19. A drill guide, comprising:

a hollow outer body extending from a proximal end to a distal end and having a slot disposed proximate the proximal end, wherein the distal end is configured as a reverse collet having a plurality of prongs;

an inner body having a central channel extending therethrough;

a spring disposed within the hollow outer body and beneath a portion of the inner body, wherein the spring biases the inner body in a direction away from the plurality of prongs;

a cap coupled to the proximal end of the hollow outer body and having a through hole disposed through an upper portion of the cap in communication with the central channel, wherein the through hole is configured to allow passage of a drill bit into the central channel;

a handle coupled to the hollow outer body to allow a user to grip the drill guide; and a lever coupled to the inner body through the slot, wherein the slot is shaped such that rotation of the lever results in the inner body moving along a central axis of the drill guide, and wherein a distal end of the inner body is configured to prevent radially inward deflection of the plurality of prongs when a distal end of the inner body is moved into a distal end portion of the hollow outer body.

20. The drill guide of claim 19, wherein the lever has a spherical shape.

* * * * *